US006187555B1

(12) United States Patent
Tautvydas

(10) Patent No.: US 6,187,555 B1
(45) Date of Patent: Feb. 13, 2001

(54) SPORES WITH INCREASED SENSITIVITY TO STERILANTS USING ADDITIVES THAT BIND TO STERILANT-SENSITIVE SITES

(75) Inventor: Kestutis J. Tautvydas, Lake Elmo, MN (US)

(73) Assignee: 3M Innovative Properties Company, St. Paul, MN (US)

( * ) Notice: Under 35 U.S.C. 154(b), the term of this patent shall be extended for 0 days.

(21) Appl. No.: 09/061,293

(22) Filed: Apr. 16, 1998

(51) Int. Cl.[7] ............................. C12N 1/00; C12N 1/20; C12N 11/10; C12N 11/14; C12Q 1/02
(52) U.S. Cl. ......................... 435/29; 435/176; 435/178; 435/180; 435/243; 435/252.1; 435/252.5; 435/822; 435/832; 435/839
(58) Field of Search ................................ 435/243, 252.1, 435/822, 4, 29, 41, 176, 178, 180, 252.5, 832, 839

(56) References Cited

U.S. PATENT DOCUMENTS

| | | | |
|---|---|---|---|
| 3,697,222 | 10/1972 | Gonzalo | 21/54 A |
| 3,968,248 | 7/1976 | Boucher | 424/333 |
| 4,883,641 | 11/1989 | Wicks et al. | 422/50 |
| 5,242,792 | 9/1993 | Rudolph et al. | 435/2 |
| 5,288,634 | 2/1994 | Harman et al. | 435/254.1 |
| 5,552,320 | 9/1996 | Smith | 435/287.4 |
| 5,739,004 | 4/1998 | Woodson | 435/31 |

FOREIGN PATENT DOCUMENTS

| | | |
|---|---|---|
| 0 156 660 A2 | 10/1985 | (EP) . |
| 0 462 460 A2 | 12/1991 | (EP) . |
| 0 638 650 A1 | 2/1995 | (EP) . |
| 0 674 845 A1 | 10/1995 | (EP) . |
| WO 94/28164 | 12/1994 | (WO) . |
| WO 95/21936 | 8/1995 | (WO) . |
| WO 96/28458 | 9/1996 | (WO) . |
| WO 97/17435 | 5/1997 | (WO) . |

OTHER PUBLICATIONS

Wolgamott et al., "Initiation of spore germination in *Bacillus cereus*: a proposed allosteric receptor", *Can. J. Microbiol.*, 17:1043–1048, 1971.
Foster and Johnstone, "Pulling the trigger: the mechanism of bacterial spore germination", *Mol. Microbiol.*, (1990), 4(1):137–141.
Shintani, "Factors in the Preparation of Biological Indicators That Affect the Decimal Reduction Time", *Biomed. Instrumentation & Technology*, (1996), 30:449–453.
Kanda et al., "Germination response of *Bacillus subtilis* PC1219 Spores to Caramelized Sugar and L–Asparagine", *J. Food Sci.*, (1991), 56(5):1339–1403.
Vary et al., "Kinetics of Germination of Bacillus Spores", *J. Bacteriol.*, (1965), 80(5):1340–1347.
Rossi et al., "Stabilization of the Restriction Enzyme EcoRI Dried with Trehalose and Other Selected Glass–Forming Solutes", *Biotechnol. Prog.*, (1997), 13:609–616.

Crowe et al., "Effects of Carbohydrates on Membrane Stability at Low Water Activities", *Biochimica et Biophysica Acta.*, (1984), 769:141–150.
Leslie et al., "Trehalose and Sucrose Protect Both Membranes and Proteins in Intact Bacteris during Drying", *Appl. Environ. Microbiol.*, (1995), 61(10):3592–3597.
Crowe et al., "Preservation of dry liposomes does not require retention of residual water", *Proc. Natl. Acad. Sci. USA*, (1987), 84:1537–1540.
Webb, "Factors Affecting the Viability of Air–Borne Bacteria", *Can. J. Microbiol.*, (1960), 6:71–87.
Webb, "Factors Affecting the Viability of Air–Borne Bacteria", *Can. J. Microbiol.*, (1960), 6:89–105.
Webb, "The Influence of Oxygen and Inositol on the Survival of Semidried Microorganisms", *Can. J. of Microbiol.*, (1967), 13(7):733–742.
Penna et al., "Thermal Resistance of *Bacillus stearothermophilus* Spores on Strips Previously Treated with Calcium", *PDA J. Pharm. Sci. Technol.*, (1996), 50(4):227–237.
Ramos et al., "Stabilization of Enzymes against Thermal Stress and Freeze–Drying by Mannosylglycerate", *Appl. Environ. Microbiol.*, (1997), 63(10):4020–4025.
Moir et al., "The Genetics of Bacterial Spore Germination", (1990), 44:531–553.
Spicher, "Sterilization—The Microbiology between Claim and Reality", *Zbl. Hyg.*, (1993), 194:223–235.
Wax et al., "Initation of the Germination of *Bacillus subtilis* Spores by a Combination of Compounds in Place of L–Alanine", *J. Bacteriol.*, (1968), 95(2):433–438.
Stumbo et al., "Nature of Thermal Death Time Curves for P.A. 3679 and *Clostridium botulinum*", *Food Tech.*, (1950), 4:321–326.
Pflug et al., "Principles of the Thermal Destruction of Microorganisms", In: *Disinfection, Sterilization, and Preservation*, (1991), 85–128, Edited by Block, Lea & Febiger.
Article: Okada et al., "Amino Acids and Peptides. III. Synthesis of Stereoisomeric Alanine Containing Peptide Derivatives and Their Effects on Germination of *Bacillus thiaminolyticus* Spores. 2," *Chem. Pharm. Bull.*, 26(11), 1978, pp. 3588–3891.

(List continued on next page.)

*Primary Examiner*—David M. Naff
*Assistant Examiner*—Deborah K. Ware
(74) *Attorney, Agent, or Firm*—James A. Rogers

(57) ABSTRACT

Microbial spores having increased sensitivity to sterilants are provided. An additive such as a dipeptide, oligosaccharide, and/or polyhydroxyalcohols are added to the spores wherein the additive is bound to sterilant-sensitive sites in the spores. The additive increases sensitivity of the spores to a sterilant. More than one additive can be utilized to alter the sensitivity of the spores to a sterilant. Biological indicators comprising the microbial spores and a solid support are also disclosed and those spores having a dipeptide specifically bound to sterilant-sensitive sites in the spores have an altered sensitivity to a sterilant. Furthermore, a method is disclosed for altering the sensitivity of microbial spores to a sterilant comprising drying the spores at a temperature between 35° C. and 55° C. in a liquid composition having an amount of the additive therein.

37 Claims, 5 Drawing Sheets

OTHER PUBLICATIONS

Abstract: Vironina et al., "Effect of Carbohydrate Nutrition on Entomophthora–Thaxteriana Growth and Spore Formation," (1982 (Recd 1983)).

Article: Sacks et al., "Increased Spore Yields of *Clostridium perfringens* in the Presence of Methylxanthines," *Applied and Environmental Microbiology,* vol. 34, No. 2, Aug., 1977, pp. 189–193.

- ● 9 mg M 8mgT 9 mg S/ml
- ○ 10 mg S/ml
- ▽ 8 mg M 8 mgT 8 mg S/ml

- ● 9 mg M 8 mgT 9 mg S/ml
- ○ 10 mg S/ml
- ▽ 8 mg M 8 mgT 8 mg S/ml

SPORES WITH INCREASED SENSITIVITY TO STERILANTS USING ADDITIVES THAT BIND TO STERILANT-SENSITIVE SITES

BACKGROUND OF THE INVENTION

The invention relates to microbial spores treated with various additives in order to alter sensitivity to sterilants.

Biological indicators (BIs) have been used to test and/or determine the effectiveness of sterilization processes. Typically, biological indicators containing microbial spores are exposed to a selected sterilant or sterilizing process and then the survival of the exposed spores is determined by placing the exposed spores in an environment capable of sustaining germination and outgrowth of spores. Microbial spores are typically more resistant to sterilization processes than most types of microorganisms and it is assumed that a sterilization process that will kill microbial spores also will kill any contaminating microorganisms.

Traditional BIs based on growth could not be used to measure directly a sterilization assurance level as low as about $10^{-1}$ and generally required incubation periods of at least two days and up to seven days before the effectiveness of the sterilization process could be assessed. The development of linear reaction velocity (LRV) technology has facilitated a sensitive method for the rapid determination of sterilization effectiveness over a wide range of frequency of survival from $10^9$ to as low as $10^{-16}$ viable spores per unit. As spores germinate, they absorb water and lose the capability of scattering light in spore-containing suspensions. This property allows the germination process to be followed spectrophotometrically as a decrease in light absorption or a decrease in light scattering. To determine spore germination rates, i.e., the decrease in absorbance per unit time, germination kinetics curves can be created by plotting the absorbance at 480 nm ("$Abs_{480}$") of a germinating spore suspension as a function of time. After spore germination is initiated, there is a lag period where little or no change in absorbance is observed. When a detectable percentage of the spores begin to germinate, a decrease in the $Abs_{480}$ of the spore suspension is observed. The decrease in the $Abs_{480}$ of the spore suspension is recorded until a majority of the spores germinate. The observed rate is affected by both the number of spores germinating and the time needed for a spore to complete germination. Thus, the more synchronous the spore germination of a given spore population, the higher the germination rate.

The LRV is the maximum spore germination rate for a particular population of spores in a particular germination medium. The LRV is computed from the descending linear portion of the germination kinetics curve that follows the lag period. The LRV is presented as the absolute value of the slope of the descending linear portion of the germination kinetics curve. Generally, LRV is expressed in units $Abs_{480}/$min. Depending on the condition of the spores and the type of germination medium used, the lag period may vary and thus the time interval representing the descending linear portion may vary. After exposing spores to a sterilant, LRVs correlate with the survival of viable spores or cells in a linear relationship. The lower the LRV, the lower the probability of non-sterile units being present in a given biological load that was subjected to a sterilization process. See, WO 95/21936, filed Feb. 15, 1995.

It has been observed that death of microorganisms within a population due to an external factor, such as heat or gas sterilants, is described best using first order kinetics, since the decrease in the number of such organisms is logarithmic. See, for example, Pflug, I. J. and R. G. Holcomb, "Principles of the thermal destruction of microorganisms", In *Disinfection, Sterilization, and Preservation*, Fourth Edition, S. S. Block, ed., Lea and Febiger, (1991), pp. 83–128. Thus, the number of organisms surviving per unit after increasingly longer exposure to a sterilant or killing treatment may be determined using the following linear regression equation (equation 1) and then plotting the calculated data on semilog graph paper.

$$\log N = -U/D + \log N_0 \qquad (eq. 1)$$

U is equal to the number of minutes of sterilant exposure. $N_0$ is equal to the number of spores or cells per unit at the beginning of the sterilization process. N is equal to the number of microorganisms remaining per unit after sterilant exposure for a given time, U. D is a decimal reduction time (specifically, minutes required to kill one log of spores or cells), which is a constant for a given set of conditions and a given batch or crop of spores or cells. Thus, D is the negative reciprocal of the slope of a straight-line death curve.

Read-out reliability (ROR) is defined as the ratio of the number of positive BIs after two days of growth compared to the number of positive BIs after 7 days of growth. For a read-out of sterilization results earlier than 7 days to be valid, an ROR of at least 97% is required. Shortening readout time is highly desirable and would enhance the effectiveness of the BI assay.

Different methods of sterilization require spores with defined levels of resistance, which likewise give rise to different D values. Not all organisms can achieve the required D values for a particular sterilization method. For example, spores from *Bacillus subtilis* are best suited for ethylene oxide (EtO) sterilization, whereas spores from *Bacillus stearothermophilus* are best suited for high temperature steam sterilization. For other sterilization methods such as hydrogen peroxide plasma, the most suitable organism has not yet been identified. It would be useful if spore resistance to a certain sterilization method could be altered to allow use of an organism when sterilization conditions change or when it is more economical to produce spores from a particular organism whose native resistance to a particular sterilization process may not be optimal.

SUMMARY OF THE INVENTION

The present invention relates to microbial spores that include one or more additives specifically bound to sterilant-sensitive sites in the spores in an amount effective for altering the sensitivity of the spores to sterilants. As used herein, an additive is a substance added to microbial spores for the purpose of altering one or more native characteristics or properties of the spores. The spores can be prepared with various resistances, i.e. various D-values, to sterilization processes, and can provide measurable LRV responses even when a sterilization assurance level of $10^{-16}$ is desired. Additives that enhance spore sensitivity can be combined with additives that decrease spore sensitivity to produce biological indicators with properties tailored to a specific sterilization method.

The invention features microbial spores that include an additive specifically bound to sterilant-sensitive sites in the spores. The additive increases the sensitivity of the spores to sterilants. As used herein, "sterilant-sensitive sites" refers to those sites within or on the spore that are necessary specifically for one or more of spore survival, germination, and outgrowth following exposure of the spores to a sterilant.

Oligosaccharides, for example trehalose, raffinose, melibiose and maltose, increase the sensitivity of the spores to a sterilant when bound to sterilant-sensitive sites in the spores and can increase read-out reliability and shorten read-out time of a biological indicator. Trehalose is a particularly useful oligosaccharide for increasing spore sensitivity.

The invention also features microbial spores that include a dipeptide specifically bound to sterilant-sensitive sites in the spores. The dipeptide alters the sensitivity of the spores to sterilants and can be stereospecifically bound to the sterilant-sensitive sites. A dipeptide bound to the sterilant-sensitive sites can decrease spore sensitivity, increase the LRV of the spores and can increase the read-out reliability of a biological indicator. Read-out time can be shortened to less than two days.

Sterilants that are useful in the invention include steam, ethylene oxide, radiation, heat, sodium hypochlorite, polyvinylpyrrolidone-iodine, sodium dichlorocyanurate, low temperature steam-formaldehyde, glutaraldehyde, hydrogen peroxide, hydrogen peroxide plasma, peracetic acid and mixtures thereof Ethylene oxide, steam and hydrogen peroxide plasma are particularly useful sterilants.

The invention also features microbial spores that include two or more additives specifically bound to sterilant-sensitive sites in the spores. The additives alter the sensitivity of the spores to sterilants and can be stereospecifically bound to the sterilant-sensitive sites. The spores can be, for example, from *Bacillus subtilis* or from *Bacillus stearothermophilus* and are typically dried. Additives bound to the sterilant-sensitive sites increase the LRV and increase the read-out reliability of a biological indicator, thereby allowing read-out times of less than two days.

Microbial spores that include two or more additives are effective for use during standard ethylene oxide cycles as well as for reduced ethylene oxide cycles. As used herein, a standard cycle of ethylene oxide sterilization employs about 60% relative humidity and a reduced cycle employs about 30% relative humidity. Spores including mannitol, trehalose and sorbitol specifically bound to sterilant-sensitive sites are particularly useful during ethylene oxide sterilization in a reduced cycle.

Microbial spores that include two or more additives effective for use during hydrogen peroxide plasma sterilization are also described. For example, spores including inositol and mannitol specifically bound to sterilant-sensitive sites can be used during hydrogen peroxide plasma sterilization. Erythritol may also be included.

The invention also relates to a method for altering the sensitivity of a microbial spore to a sterilant. The method includes drying the spores in a liquid composition that includes an additive in an amount effective to alter sensitivity of microbial spores to a sterilant when the additive is specifically bound to sterilant-sensitive sites in the spores. The spores are dried at a temperature between about 35° C. and about 55° C., preferably from about 45° C. to about 50° C.

Additives that are useful in the method may increase or decrease the sensitivity of the spores to a sterilant. Oligosaccharides, for example, trehalose, raffinose, melibiose and maltose, increase the sensitivity of spores to a sterilant when bound to sterilant-sensitive sites in the spores. Trehalose is a particularly useful oligosaccharide for increasing spore sensitivity. Polyhydroxy alcohols and dipeptides, for example, inositol, mannitol, adonitol, erythritol and L-carnosine decrease the sensitivity of the spores to a sterilant when specifically bound to sterilant-sensitive sites within the spore. Spores containing such additives have an increased read-out reliability, allowing read-out times of less than two days.

In another aspect, the invention features a biological indicator that includes microbial spores and a solid support to which the spores are attached. The spores include a dipeptide or two or more additives specifically bound to sterilant-sensitive sites in the spores that alter sensitivity of the spores to a sterilant.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
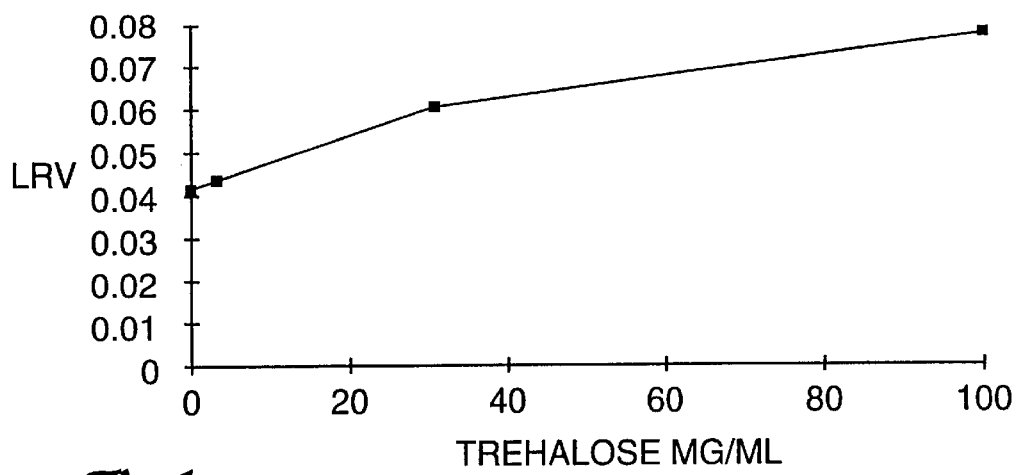
FIG. 1 is a graph that depicts the LRV of spores dried in the presence of varying concentrations of trehalose.

In one aspect, the invention features microbial spores including one or more additives specifically bound to sterilant-sensitive sites in the spores. The bound additives alter the sensitivity of the spores to a sterilant. Such additives can be identified using the methods and concepts described herein. Specifically, additives are identified by treating microbial spores with various additives prior to drying and then testing for altered sensitivity to sterilants. For example, the D value or amount of time required to kill one log of spores may be increased or decreased by various additives.

Sterilant-sensitive sites refers to those sites that are necessary specifically for one or more of spore survival, germination and outgrowth following exposure of the spores to a sterilant and may include various proteins or other biological macromolecules. Binding of the additives to the sterilant-sensitive sites may alter the accessibility of the sites to various sterilants or may alter the sterilant-sensitivity through other mechanisms. Additives are bound to the sterilant-sensitive sites within or on the spores when an increase or decrease in spore resistance to sterilants is observed. Some additives bind to the sterilant-sensitive sites stereospecifically. Stereospecific binding of the additives to sterilant-sensitive sites is present when the stereochemistry of the additive affects the sterilant sensitivity of the spores. For example, stereospecific binding is present when differential sterilant sensitivity effects are attributable to enantiomers, diastereoisomers or epimers of an additive.

Microbial spores that are useful in the invention include any spore commonly used to monitor sterilization processes. For example, spores from *Bacillus subtilis, Bacillus circulans, Clostridium perfringens, Clostridium sporogenes* or *Bacillus stearothermophilus* are useful. Spores from *Bacillus subtilis,* American Tissue Culture Collection (ATCC) accession number 9372, and *Bacillus stearothermophilus,* ATCC accession number 8005 or ATCC accession number 7953, are particularly useful. The spores can be unpurified or purified. For example, *B. subtilis* spores can be separated into heavy and light spores by differential centrifugation of an aqueous suspension. Heavy spores pellet after centrifuigation for 12 to 15 minutes at 2,000×g, whereas the light spores remain in suspension. The light spores can be pelleted by centrifugation of the supernatant from the first centrifugation for 30 minutes at 2,000×g, The heavy spores can be further purified by filtering a dilute suspension of heavy spores through Whatman GF/D glass fiber filters to remove bits of agar, denatured nucleoproteins and other debris that sediments with the spores in the first centrifugation. Spore viability does not change when unpurified, heavy or light spores are used, although the slope of the EtO exposure time/LRV response curve is steeper when unpurified or heavy spores are used.

The spores can be in suspension or can be dried. The spores can be dried on a carrier such as paper, plastic, glass or metal, that is suitable for use in a biological indicator. Drying the spores in the presence of the additives aids the penetration of various additives into the spores and the subsequent binding to sterilant-sensitive sites. Dried spores that include one or more additives specifically bound to sterilant-sensitive sites within or on the spores can be prepared by treating spore suspensions with a single additive or a combination of additives and then drying an aliquot for a sufficient period of time at a temperature between about 35° C. and about 55° C. Preferably, the drying temperature is between about 45° C. and 50° C. and more preferably, between about 47° C. and about 48° C. For example, a suspension of treated spores can be dried down in four hours at about 48° C. Spores dried in this manner appear dry on the surface, but likely retain a residual amount of bound water within the spore. Alternatively, the spore suspension can be dried onto a carrier for about 12–20 hours at about 37° C.

As used herein, "sterilant" refers to any method of sterilization. For example, steam, ethylene oxide, radiation, heat, sodium hypochlorite, polyvinylpyrrolidone-iodine, sodium dichlorocyanurate, low temperature steam-formaldehyde, glutaraldehyde, hydrogen peroxide, hydrogen peroxide plasma, peracetic acid and mixtures thereof are sterilants that are useful in the invention.

In one embodiment, the microbial spores include additives that increase the sensitivity of the spores to the sterilant. Non-limiting examples of additives that increase spore sensitivity include oligosaccharides such as trehalose, raffinose, melibiose, and maltose. Preferably, the oligosaccharide is trehalose.

Adding carbohydrates such as trehalose or sucrose prior to drying and freezing serves to stabilize biological samples such as microorganisms and enzymes that are typically damaged during drying and freezing processes. Leslie, S. B. et al., (1995), *Appl. Environ. Microbiol.,* 61(10):3592–3597. Proteins in a dry state may be damaged by free radicals that accumulate in organisms during severe dehydration. Phospholipid bilayers may be damaged by removal of hydrogen-bonded water from the headgroup region of the bilayer, causing the bilayer to undergo a phase transition from liquid crystalline to gel phase. During rehydration, dry membranes cannot transition back to liquid crystal completely, resulting in packing defects and leaky membranes. Carbohydrates may lower the transition temperature of dry membranes by replacing water between lipid headgroups, thus preventing the phase transition and the accompanying leakage upon rehydration. Trehalose was found to be highly effective at preserving membranes in low water states, while sugar alcohols were least effective. Crowe, L. M. et al., (1984), *Biochim. Biophys. Acta.,* 769:141–150. Intracellular proteins are thought to be protected in a hydrated conformation formed by binding of carbohydrates to hydrophilic protein domains and preventing inter- and intraprotein hydrogen bonding.

Surprisingly, addition of trehalose to spore suspensions prior to drying and exposure to EtO enhanced spore germination rates and decreased spore survival after exposure to EtO. As such, trehalose used in this fashion increased the sensitivity of spores to EtO sterilization. In general, spore germination is triggered through the binding of germinants, such as the amino acids L-alanine and related amino acids, or L-asparagine and L-glutamine in the presence of glucose, fructose and potassium ($K^+$), to specific receptor sites in or on the spore membrane. An increase in germination rate can indicate that more spores are germinating at the same time or that the germination of individual spores is faster, or both. In other words, trehalose and other additives with similar properties synchronize spore germination and outgrowth of the spore cell. Without being bound by any particular mechanism, the additives may increase the penetration of germination medium and the number of available germinant binding sites. Similarly, since spore death occurs when EtO alkylates vital components or viability factors within the spore, an increase in spore death after EtO exposure of trehalose treated spores can result from an increased accessibility of EtO to viability factors and a corresponding increase in alkylation.

Treatment of spores with trehalose or other compounds with similar properties can lead to an increase in spore germination and a reduction in the number of spores that germinate late and grow out slowly upon addition of growth medium. Trehalose and other additives with similar properties can enhance the readout reliability and shorten the read-out time to less than two days of biological indicators whose readout is based on growth, and ensure a better correlation between rapid readout assays and outgrowth results. Trehalose and other additives with similar properties can improve the reliability of biological indicators by increasing the steepness of the EtO exposure time/LRV response curve.

In another embodiment, the spores include one or more additives that decrease the sensitivity of the spores to the sterilant. Read-out reliability of a biological indicator is increased in spores containing such additives. The time to achieve a read-out reliability of 97% or greater is shortened to less than two days. Additives that decrease spore sensitivity and thus increase spore resistance to sterilants include, for example, polyhydroxy alcohols such as sugar alcohols and cyclitols, and dipeptides. In particular, the additive can be myo-inositol, D-mannitol, adonitol, meso-erythritol or L-carnosine. Related forms, such as L-forms of mannitol or other meso forms of inositol and erythritol, also are expected to have an effect on spore resistance and can be identified using the techniques described herein. Each additive can decrease spore sensitivity through a stereospecific effect, as additives containing the same number of carbons do not necessarily provide the same degree of spore protection or resistance.

The invention also features microbial spores including one or more additives that are effective for use in a standard cycle as well as in a reduced cycle. Preferably, the spores include mannitol, trehalose and sorbitol. For a BI to be valid, it must indicate failure under non-optimal sterilization conditions. Sterilization cycles may fail because gas concentration, temperature or relative humidity are inadequate. Preconditioning spores with additives that include mannitol, trehalose and sorbitol obtains the desired spore resistance to EtO at optimal relative humidity in a standard EtO cycle, i.e. 60%, while maintaining a normal germination rate response, and increased resistance in reduced or non-optimal sterilization cycles such as 30% relative humidity.

The invention also features microbial spores that are effective for use during hydrogen peroxide plasma sterilization. Such spores contain additives such as inositol and mannitol and optionally erythritol. Spores from *B. subtilis* are particularly useful as they are easy to produce and have an excellent LRV response.

In another aspect, the invention features a liquid composition that includes one or more additives in an amount effective to alter sensitivity of microbial spores to a sterilant when the additives are specifically bound to sterilant-sensitive sites in the spores. The compositions can include one or more additives that increase or decrease sensitivity as discussed above. Liquid compositions including one or more additives that decrease the sensitivity of the spores to the sterilant can increase the read-out reliability and shorten the read-out time of biological indicators to less than two days. Microbial spores that are useful in the invention can be any spore commonly used to monitor sterilization processes.

The liquid composition can also include one or more additives that are effective for use at about 30% relative humidity during ethylene oxide sterilization. The composition can include mannitol, trehalose and sorbitol. The sorbitol concentration of the composition is typically from about 7 mg/ml to about 9 mg/ml, e.g., about 8 mg/ml. The mannitol and trehalose concentrations can vary from about 7 mg/ml to about 10 mg/ml, with the trehalose concentration usually being less than or equal to the sorbitol concentration.

The invention also features a liquid composition that includes one or more additives that are effective for hydrogen peroxide plasma sterilization. The composition includes various additives such as inositol and mannitol, and optionally erythritol. The concentration of inositol in the composition typically ranges from about 1 mg/ml to about 5 mg/ml and the concentration of mannitol in the composition typically ranges from about 5 mg/ml to about 10 mg/ml. The concentration of erythritol can vary from about 0.5 mg/ml to about 1 mg/ml.

Generally, the spores are preconditioned by drying in the presence of the liquid composition. Following drying, the spores can be used to produce biological indicators, typically by immobilizing the dried spores on a solid support. The solid support can be, for example, a cuvette or container that retains the spores. Suitable cuvette or container materials include quartz glass or a variety of polymeric materials such as poly(methylmethacrylate) or polystyrene. Alternatively, the solid support can be metal, plastic, glass, paper or one or more membranes to which the microbial spores are attached. For example, the spores can be immobilized between two membranes to prevent loss of the spores from the membrane.

The invention will be further described in the following examples, which do not limit the scope of the invention described in the claims.

EXAMPLES

Example 1

Increased Spore Germination Rates by Addition of Oligosaccharides

Trehalose or other similar compounds were added at various concentrations to *B. subtilis* spores suspended in water. Twenty microliters of the treated spore suspensions, approximately $1.2 \times 10^8$ spores, were added to polymethacrylate semimicro cuvettes and then dried for 4 hours at 48° C. After drying, 1.2 ml of germination medium containing 75 mM L-asparagine or L-glutamine with approximately 0.03%–0.06% L-alanine as a contaminant (Aldrich), 1.67 mM fructose, 1.67 mM glucose, 0.2 M KCl, 0.1 M NaCl and 0.1 M phosphate buffer (6.95 g $KH_2PO_4$/L+6.95 g $Na_2HPO_4$/L, pH 7.25 at 22° C.) were added to each cuvette. Spores were resuspended by vortexing for 10 seconds. Spore germination was determined by recording the change in absorbance of light at 480 nanometers in a Cary/Varian spectrophotometer. The maximum germination rate or LRV was calculated from the germination kinetics curves. The experiments were done with trehalose, raffinose, maltose and melibiose and were repeated at least twice.

The results of a typical response of spores to trehalose treatment are shown in FIG. 1. Each data point is the average of four replications with the standard deviation typically 1 to 5%. As the concentration of trehalose was increased from 0 to 100 mg/ml per spore suspension, there was a concomitant increase in the LRV. Similar results were obtained with all of the tested compounds and with three different spore crops. It was surprising to find that all tested compounds substantially increased the germination rates of spores that were dried in the presence of the compounds. The additives had no effect when included only in the germination medium and then tested on spores dried in the absence of any additive.

Example 2

Enhanced Spore Sensitivity to EtO Sterilization

Spores were prepared in the same manner as in Example 1. After drying, the spores were exposed to EtO in a Joslyn-B.I.E.R. sterilization vessel for various times using standard cycle conditions of 15 minutes preheat at 54.5° C., 30 minutes incubation at 60% relative humidity (R.H.), EtO exposure at a concentration of 600 mg EtO/L of air, three deep vacuum cycles of about 3 minutes and 1 minute aeration in the vessel. The source of the EtO was a standard mixture of 12% EtO and 88% Freon (12/88 gas). The cuvettes with the spores were then removed from the sterilization chamber and allowed to aerate overnight, approximately 20 hours at room temperature, before resuspending in germination medium and determining the LRV response. The results of a typical experiment are shown in FIG. 2.

Figure 2:
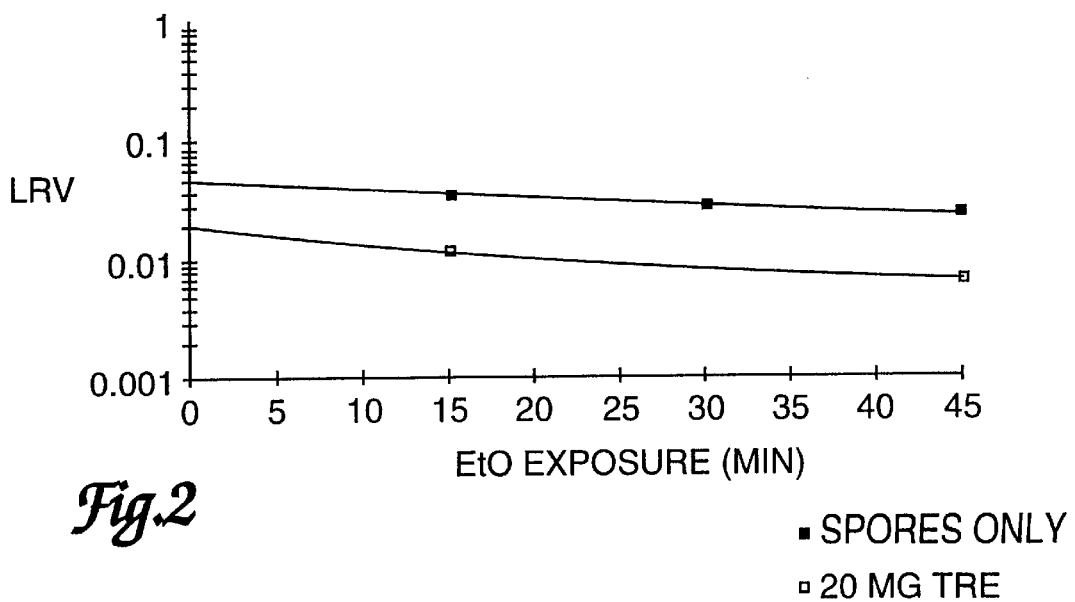
FIG. 2 is a graph that depicts the LRV of spores dried in the presence of varying concentrations of trehalose and subsequently exposed to EtO.

As shown in FIG. 2, the LRV response was suppressed substantially in spores that were dried in the presence of trehalose. Other oligosaccharides that increased spore germination like trehalose also showed reduced LRV responses, but their effects on the steepness of the EtO exposure time/LRV response curves varied.

Trehalose and other similar compounds were tested for their effects on the survival of spores (outgrowth) after EtO exposure. Spores were prepared and treated in the same manner as described above. Approximately 50 to 100 cuvettes per treatment were used in these experiments.

EtO exposures were timed to give positive growth in about 50% of cuvettes, but varied from 0 to 100% in different experiments. After the aeration period, one ml of a sterile growth medium was added aseptically to each cuvette. The cuvettes were then capped with sterile parafilm, and incubated at 37° C. for 7 days. At one, two and seven days of growth, the number of cuvettes positive for growth as indicated by appearance of turbidity, were counted and ROR and D-EtO values were determined for each treatment. D values were calculated as per the Stumbo, Murphy, Cochran method. Stumbo, C. R., et al., (1950), *Food Tech.*, 4:321–326. The results of these studies are summarized in Table 1.

TABLE 1

| Additive | mg/ml | % Resusp. | Y intercept | St. Index | min. EtO | D value |
| --- | --- | --- | --- | --- | --- | --- |
| None | 0 | 73 | 0.0502 | 6.9 | 17 to 20 | 2.16 |
| Trehalose | 20/3 | 96 | 0.0239 | 9.3 | 12 to 14 | –/1.55 |
| Raffinose | 20 | 94 | 0.033 | 2.5 | 12 | 1.5 |
| Melibiose | 20 | 95 | 0.03 | 2.4 | 14 | 1.5 |
| Maltose | 20 | 95 | 0.01 | 6.7 | 14 | 1.7 |

In Table 1, the "y intercept" (of the EtO exposure time/LRV response curves) gives the LRVs for the spores before exposure to EtO but subjected to the preheat and R.H. dwell times. "St. (steepness) index" is a measure of the steepness of the EtO exposure time/LRV response curves obtained by dividing the LRV response at 0 minutes EtO by the LRV response at 60 minutes EtO. The "min. EtO" column gives the minutes of EtO exposure of the spores.

Trehalose, raffinose, melibiose and maltose were found to be completely inert for spore germination when included only in the germination medium, but did increase spore resuspension up to 96% (Table 1) when present during drying of the spores. Typically, if no water soluble compound is added to spores before drying, spore resuspension is about 70% with most crops of spores, but can be far lower. The more soluble the compound was in water, the more effective it was in facilitating spore resuspension.

The results in Table 1 indicate that the compounds affected the sensitivity of the spores to EtO to varying degrees. Desirable effects of these additives include a steeper EtO exposure time/LRV response curve than control and an initial LRV (y intercept) greater than 0.02. Of the oligosaccharides tested, trehalose had the best combination of these two characteristics. Trehalose provided the greatest decrease in spore resistance as it gave the greatest reduction in D Eto values. The D value was measurable only when the concentration of trehalose was reduced to 3 mg/ml. At higher concentrations, trehalose treated spores did not survive exposure to EtO even with short exposure times. Thus trehalose, like the other oligosaccharides tested, increased the sensitivity, or lowered the resistance of the spores to EtO.

Another surprising effect of the oligosaccharides, as well as the polyhydroxyalcohols and dipeptides, was that the time required for read-out of survival results was shortened. ROR percentage of spores treated with trehalose and the other oligosaccharides tested was at least 97% on day two of growth and often greater than 97% on day one of growth regardless of the percent survival. For the controls, ROR was 97% or greater on day two of growth only when the number of cuvettes positive for growth was 40% or greater. Furthermore, a ROR of greater than 90% on day one of growth was seldom achieved with the controls. This unexpected result indicates that trehalose and other compounds that affect spore resistance may cause a synchronization of the spore population for growth as well as for germination and response to sterilants. This discovery makes it possible to shorten the read-out time from two days to one day for BIs based on outgrowth.

Trehalose also preserves *B. stearothermophilus* spores for a minimum of a few months. Spores dried in trehalose can be resuspended, without loss of resuspension efficiency, after storage for a few months. Spores dried in water show a progressive decrease in resuspension efficiency. This indicates that spores as well as cells dried in trehalose are better preserved than spores dried without trehalose.

Example 3

Figure 3:
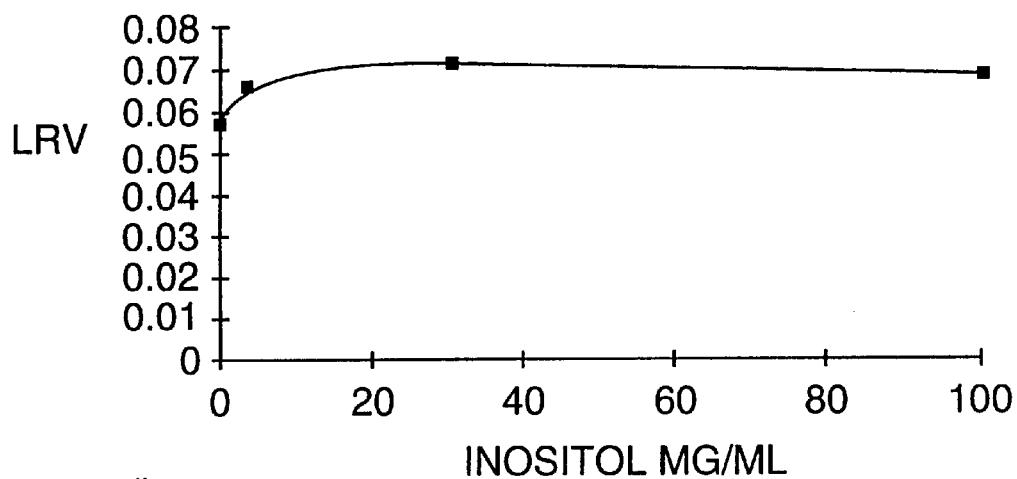
FIG. 3 is a graph that depicts the LRV of spores dried in the presence of varying concentrations of myo-inositol.
Figure 4:
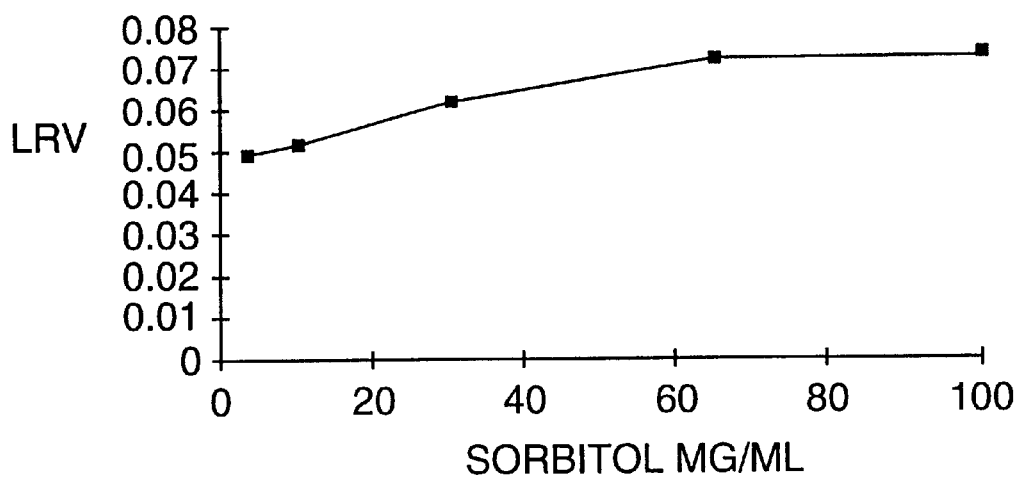
FIG. 4 is a graph that depicts the LRV of spores dried in the presence of varying concentrations of D-sorbitol.

Increased Spore Germination Rates by Addition of Polyhydroxy Alcohols (Sugar Alcohols and Cyclitols) and Dipeptides The compounds to be tested were added at various concentrations to *B. subtilis* spores suspended in water. Twenty microliters of the treated spore suspensions, approximately $1.2 \times 10^8$ spores, were added to polymethacrylate semimicro cuvettes and then dried for 4 hours at 48° C. After drying, 1.2 ml of germination medium as described in Example 1, was added to each cuvette and the spores were resuspended by vortexing for 10 seconds. Spore germination was determined by recording the change in absorbance of light at 480 nanometers in a Cary/Varian spectrophotometer. The maximum germination rate or LRV was calculated from the germination kinetics. The experiments were done with D-sorbitol, myo-inositol, D-mannitol, adonitol, meso-erythritol, and L-carnosine and were repeated at least twice. The results of a typical LRV response of spores dried in the presence of the tested compounds is shown in FIG. 3 for inositol and FIG. 4 for sorbitol. Each data point was the average of four replications with the standard deviation typically 1 to 5%.

As was observed with the oligosaccharides, the polyhydroxyalcohols increased the LRV of spores dried in the presence of these compounds, although the LRV response of the spores saturated at a much lower concentration of compound. As with trehalose, the increase in the germination rate may be due to the opening up of sites required for binding of germination triggering components of the germination medium. Consequently, the LRV is faster because the spores are germinating more synchronously.

Example 4

Reduced Spore Sensitivity to EtO Sterilization

Figure 5:
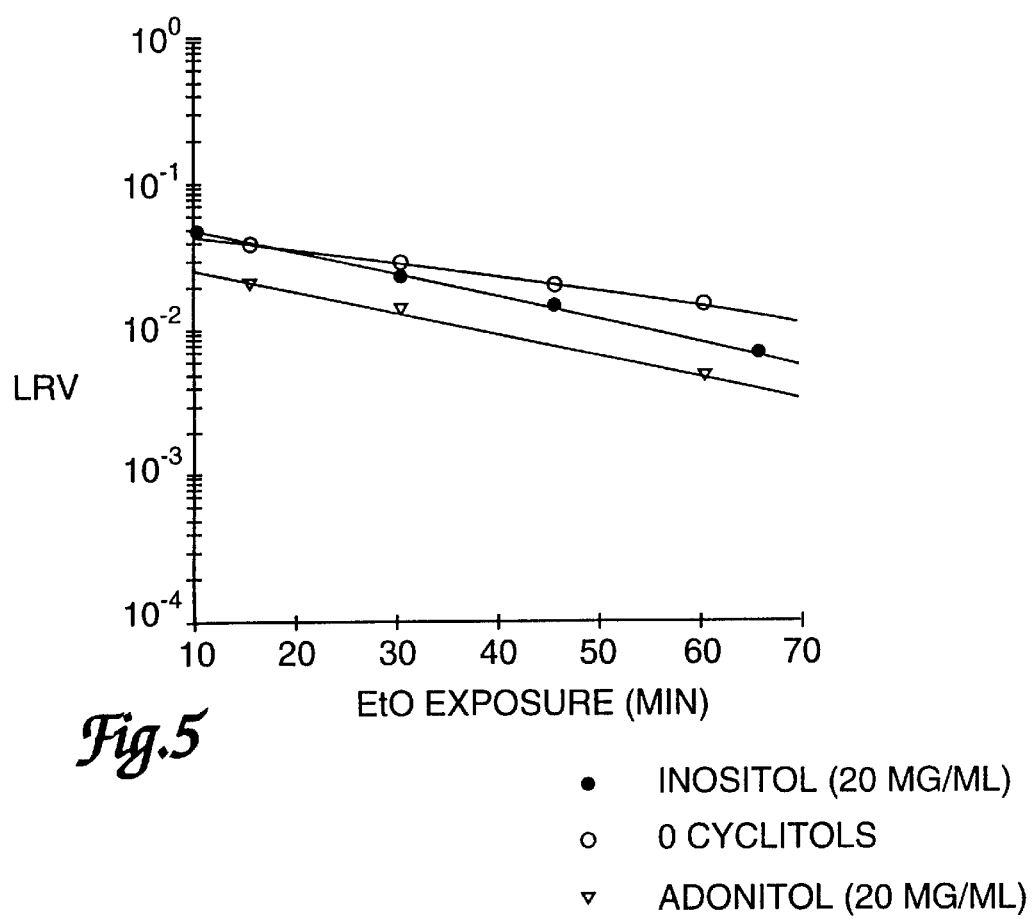
FIG. 5 is a graph that depicts the LRV of spores dried in the absence of cyclitols or other polyhydroxy alcohols (open circles) and in the presence of myo-inositol (filled circles) and adonitol (open triangles) and subsequently exposed to EtO in a standard cycle with 60% relative humidity.
Figure 6:
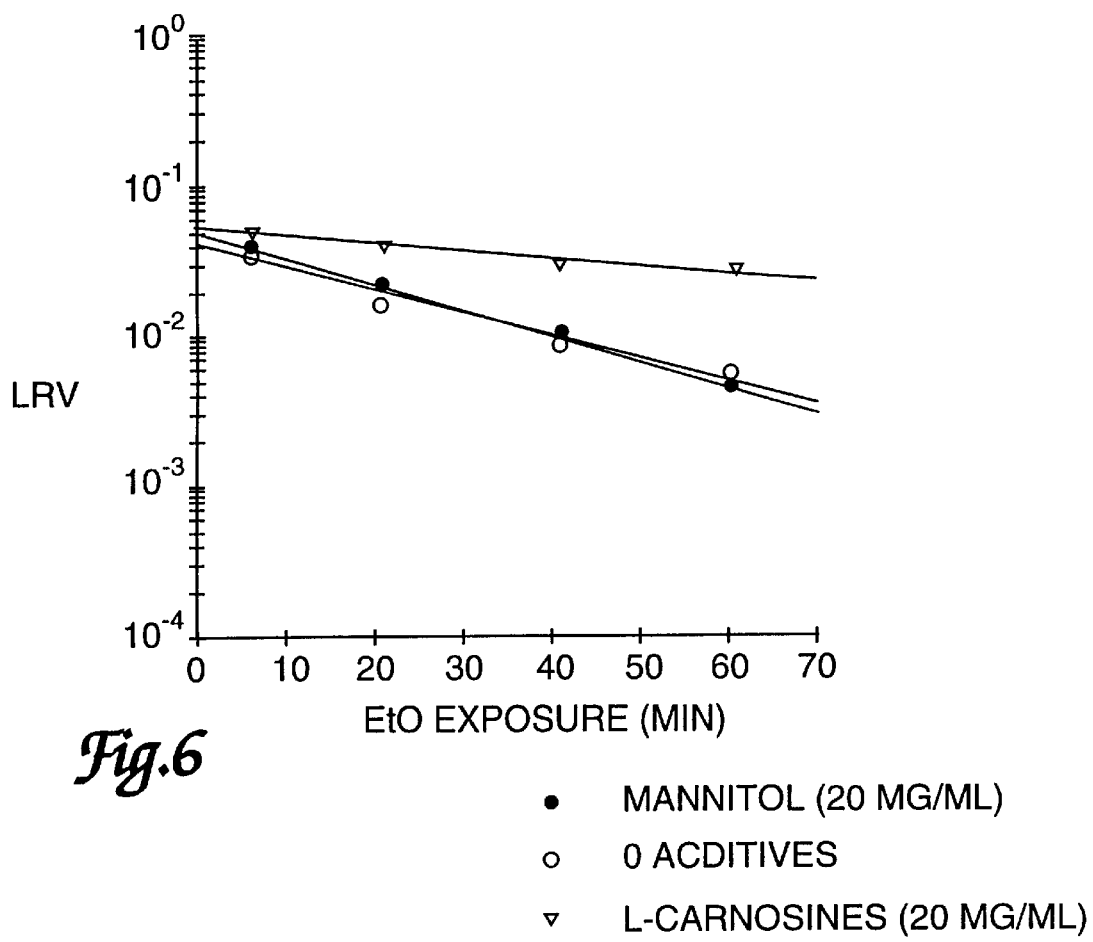
FIG. 6 is a graph that depicts the LRV of spores dried in the absence of cyclitols or other polyhydroxy alcohols (open circles) and in the presence of D-mannitol (filled circles) and L-carnosine (open triangles) and subsequently exposed to EtO in a standard cycle with 60% relative humidity.

In this example, the spores were prepared in the same manner as in Example 3. After drying, the spores were exposed to EtO in a Joslyn-B.I.E.R. sterilization vessel for various times using standard cycle conditions as described in Example 2. After EtO exposure, the spores were removed from the sterilization chamber and allowed to aerate approximately 20 hours at room temperature, before resuspending in germination medium and determining LRV responses. The results of typical experiments are shown in FIGS. 5 and 6.

As shown in the graphs, the LRV decreased linearly with increasing time of exposure to EtO in all the treatments. Compounds such as L-carnosine and meso-erythritol (see The effects of polyhydroxy alcohols on the survival (as indicated by outgrowth) of spores after exposure to ethylene oxide was also tested. Spores were prepared and treated in the same manner as described above. Approximately 50 to 100 cuvettes per treatment were used in these experiments. EtO exposures were timed such that approximately 50% of the cuvettes were positive for growth, although the number of cuvettes showing positive growth signs varied from 0 to 100% in different experiments. After the aeration period, one ml of growth medium was aseptically added to each cuvette. The cuvettes were capped with sterile parafilm and incubated at 37° C. for 7 days. At one, two and seven days of growth, the number of cuvettes positive for growth were counted and ROR and $D_{EtO}$ values were determined for each treatment. The D values were calculated per the Stumbo, Murphy, Cochran method as described in Example 2. Table 2 is a summary of the results of several experiments.

TABLE 2

| Additive | Y Int | Slope (−) | COEF Deter | St. Ind. | mg/ml | Min EtO | D EtO |
|---|---|---|---|---|---|---|---|
| None | 0.0502 | 0.0138 | 0.9934 | 6.9 | 0 | 17–20 | 2.16 |
| myo-Inosit | 0.0598 | 0.0161 | 0.9933 | 9.4 | 20, 10, 3/1 | 60 | ~/7.92 |
|  |  |  |  |  | 20/3 | 120 | ~/15.35 |
| L-Carnos | 0.0491 | 0.0064 | 0.9985 | 2.4 | 20, 10,3/1 | 60–120/60 | ~/7.98 |
| D-Mannit | 0.0485 | 0.0155 | 0.9981 | 9.5 | 20, 10/3/1 | 60 | ~/7.25/6.58 |
| meso-Eryth | 0.0285 | 0.0066 | 0.968 | 2.5 | 20 | 18–22 | 2.8 |
| Adonitol | 0.0368 | 0.0152 | 0.9938 | 8 | 20 | 18–19 | 2.35 |
| D-Sorbitol | 0.048 | 0.0215 | 0.9954 | 20.1 | 20/20 | 16/18–19 | 1.89/1.97 |
| Trehalose | 0.0239 | 0.0156 | 0.9911 | 9.3 | 3.0/3.0 | 10/12–14 | 1.27/1.49 |

Tables 2 and 3) decreased the slope of the response curve. Other compounds, such as D-mannitol and myo-inositol, increased the slope slightly, while compounds such as D-sorbitol increased the slope of the LRV response curve dramatically. It is possible that some of the effects of the additives on LRV are due to different responses of the two germination systems believed to exist in *B. subtilis* spores. See, Foster, S. J. and K. Johnstone, (1990), *Mol. Microbiol.*, 4(1):137–141. An increase in the steepness of the LRV response curve may be an indication that the compound in question had increased the sensitivity of the L-alanine activated germination system to EtO, the system normally insensitive to EtO but still activated somewhat in the germination medium used. A decrease in the steepness of the LRV response curve may be an indication that the compound in question had increased the sensitivity of the L-asparagine, glucose, fructose and potassium (AGFK) activated germination system to EtO, the system normally sensitive to EtO. See, for example, WO 95/21936, filed Feb. 15, 1995.

Although the effects of these compounds on the LRV response of spores before exposure to EtO was more or less the same, spores dried in the presence of equal concentrations of these compounds and then exposed to EtO showed individual differences, indicating specificity in how the compounds affected the sensitivity of the spores to EtO alkylation. These differential effects were found to be even more dramatic in the case of spore survival after exposure to EtO, as shown in Tables 2 and 3.

In Table 2, the mean values of the y int. (y-intercept), the negative (−) slope, and coefficient of determination columns were obtained from regression analyses of the EtO exposure time/LRV response curves of the type shown in FIGS. 5 and 6. The concentrations of the additives used to precondition the spores in the LRV determination after EtO exposure were 10 or 20 mg/ml. Steepness Index (St. Ind.) data were obtained by dividing the LRV response at 0 minutes of EtO exposure (y-intercept) during the sterilization cycle by the LRV response at 60 minutes of EtO exposure. These data are equivalent in type to the slope of the curves but give added information on the drop in germination rate occurring in response to exposure of the spores to EtO, facilitating the comparison of slopes from different treatments. The mg/ml column represents the concentrations of the additives used for pre-conditioning the spores in the experiments for determining D values. A "~" indicates that a D-value could not be determined because all of the cuvettes showed outgrowth. The Min. EtO are the minutes of EtO exposure during the sterilization cycle.

As shown in Table 2, the LRVs (see y intercepts) of spores treated with erythritol, adonitol, and trehalose were reduced after exposure to EtO relative to the other treatments. Yet, the D values of the spores treated with these compounds, with the exception of trehalose, were greater than those of the controls (0 additives) and with some compounds, such as myo-inositol, L-carnosine and D-mannitol, EtO failed to kill all the spores, even with as little as 1 mg/ml of the compounds. Measurable D values were obtained only when the concentration of myo-inositol, D-mannitol, and L-carnosine were decreased to 3 mg/ml or less, the time of EtO exposure was increased to 60 minutes or more, or both. These results indicate that the vital sites responsible for spore viability and outgrowth of the spore cell are different from the germinant binding sites involved in the germination systems. Accessibility or sensitivity to EtO, and most likely other sterilizing agents, can be profoundly affected by treatment of spores with the compounds tested here and other compounds with similar properties. Thus, the resistance of spores to EtO and other methods of sterilization can be increased or decreased over a very wide range from lower resistance than untreated spores to essentially complete resistance. The additives can be ranked in the following order of protection of B. subtilis spores (highest to lowest): myo-inositol, L-carnosine, D-manhitol, meso-erythritol, adonitol and D-sorbitol. Myo-inositol and L-carnosine provided approximately the same degree of resistance and were the most active. Meso-erythritol and adonitol provided significantly less protection than the other additives, while D-sorbitol had no effect on the D-value of the spores.

Thus, the protection of spores against alkylation with EtO varied with the additive. Some additives were far more effective than others in providing protection. It was surprising to find that the D values of spores treated with myo-inositol, D-mannitol and D-sorbitol, all six carbon polyhydroxy alcohols that differ from each other simply by the stereo position of one hydroxyl group, were so vastly different. This degree of specificity indicates that these additives may be entering and occupying or binding to the sites vital for spore survival, germination and outgrowth and in that way preventing EtO from alkylating the OH, SH, NH, or COO groups of proteins or other biological molecules. The fact that both myo-inositol and L-carnosine (N-beta-alanyl-L-histidine), a cyclitol and a dipeptide, provided essentially the same level of protection but different effects on LRV, supports the conclusion that the viability factors are at different sites than the germination sites and that the mechanism of action of these compounds involves molecular volume and charge on the molecule, among other things. The increased resistance of spores to EtO cannot be due to simple scavenging or non-specific blockage of EtO as when dried spores are coated with immobilizing agents, or to a repair mechanism after EtO alkylation. Inclusion of inositol in the spore outgrowth medium over a wide concentration range showed essentially no effect on the outgrowth of spores exposed to EtO.

Example 5

Increased Resistance at 30% Relative Humidity with Single Additives

This example shows the effect of pretreating or preconditioning spores with additives on the LRV response to EtO exposure in a standard cycle (60% RH) and in a reduced cycle (30% RH). As with any BI, to validate the prototype of the spore germination or LRV biological indicator product, it is necessary to show that the BI would indicate failure, i.e., an increase in parameter measured, when attempting to sterilize at lower than required relative humidity or EtO concentration. As a test of a BI response to an incomplete or reduced cycle, it is standard practice to use a lower humidity level, such as 30%, as opposed to optimal RH levels of 60%. It is common knowledge that reduced cycles give higher survival or higher D values than a normal cycle. In a normal cycle at 60% RH, the LRV response curve is typically a straight line with a negative slope of at least 0.015. In a reduced cycle with 30% RH, the slope should be much less steep, about 0.01 or less, and the LRV readings should be higher. For example, if the normal LRV response at 30 minutes is about 0.01 units/minute, indicating that sterilization was complete, at 30% RH, the LRV should be at least 0.015 units/min, indicating failure.

Table 3 summarizes the results of four EtO exposure experiments at 60% RH. Tables 4 and 5 summarize the results of EtO exposure at 30% RH. The mean LRV values and standard deviations are reported. In these experiments, the standard gas cycle had a 15 minute heat equilibration period, a 30 minute RH equilibration period, an EtO period of variable length, three deep vacuum cycles of about 3 minutes and a one minute aeration in the chamber. In these experiments, the additives were used individually to precondition the spores during drying.

TABLE 3

60% Relative Humidity

| EtO Min | MEAN | STDEV | % ST DEV | Eto Min | MEAN | STDEV | % ST DEV |
|---|---|---|---|---|---|---|---|
| NO ADDITIVES | | | | NO ADDITIVES | | | |
| 5 | 0.0427 | 0.00072 | 1.68 | 5 | 0.0337 | 0.00133 | 3.94 |
| 20 | 0.0283 | 0.0008 | 2.83 | 20 | 0.0151 | 0.00081 | 5.43 |
| 40 | 0.0177 | 0.00184 | 10.43 | 40 | 0.077 | 0.00026 | 3.4 |
| 60 | 0.0075 | 0.00032 | 4.28 | 60 | 0.005 | 0.00065 | 13.03 |
| 20 mg/ml MANNITOL | | | | 20 mg/ml MANNITOL | | | |
| 5 | 0.0444 | 0.0023 | 5.19 | 5 | 0.0359 | 0.00182 | 5.09 |
| 20 | 0.0309 | 0.00103 | 3.33 | 20 | 0.0199 | 0.00164 | 8.22 |
| 40 | 0.0146 | 0.00053 | 3.67 | 40 | 0.009 | 0.00072 | 8.0 |
| 60 | 0.0068 | 0.00057 | 8.41 | 60 | 0.0039 | 0.00066 | 17.1 |
| 20 mg/ml SORBITOL | | | | 20 mg/ml L-CARNOSINE | | | |
| 5 | 0.0304 | 0.00234 | 7.7 | 5 | 0.0436 | 0.00107 | 2.46 |
| 20 | 0.0175 | 0.00048 | 2.74 | 20 | 0.0359 | 0.00108 | 3 |
| 40 | 0.007 | 0.00046 | 6.61 | 40 | 0.0275 | 0.00133 | 4.86 |
| 60 | 0.0023 | 0.00021 | 9.39 | 60 | 0.0232 | 0.00068 | 2.96 |
| | | | | 20 mg/ml ERYTHRITOL | | | |
| | | | | 5 | 0.0216 | 0.0078 | 3.61 |
| | | | | 20 | 0.0163 | 0.00064 | 3.92 |
| | | | | 40 | 0.0138 | 0.00046 | 3.33 |
| | | | | 60 | 0.0177 | 0.00068 | 5.81 |
| NO ADDITIVES | | | | 10 mg/ml TREHALOSE | | | |
| 5 | 0.0343 | 0.00099 | 2.91 | 5 | 0.025 | 0.00071 | 2.86 |
| 30 | 0.0169 | 0.00026 | 1.56 | 30 | 0.0088 | 0.00076 | 8.6 |
| 60 | 0.0076 | 0.0011 | 14.6 | 60 | 0.0023 | 0.00045 | 19.77 |
| NO ADDITIVES | | | | 20 mg/ml myo-INOSITOL | | | |
| 5 | 0.0408 | 0.00256 | 6.29 | 5 | 0.0437 | 0.00158 | 3.61 |
| 20 | 0.0283 | 0.00148 | 5.23 | 20 | 0.0295 | 0.00117 | 3.97 |
| 40 | 0.0156 | 0.00148 | 9.47 | 40 | 0.0155 | 0.00113 | 7.29 |
| 60 | 0.0068 | 0.0007 | 10.37 | 60 | 0.0052 | 0.00054 | 10.38 |
| 20 mg/ml ERYTHRITOL | | | | | | | |
| 5 | 0.0251 | 0.0037 | 14.73 | | | | |
| 20 | 0.0176 | 0.00053 | 3.05 | | | | |
| 40 | 0.015 | 0.00083 | 5.42 | | | | |
| 60 | 0.0124 | 0.00096 | 7.81 | | | | |

TABLE 4

30% Relative Humidity, Reduced Cycle

| EtO Min | MEAN | STDEV | % ST DEV | EtO Min | MEAN | STDEV | % ST DEV |
|---|---|---|---|---|---|---|---|
| NO ADDITIVES | | | | 20 mg/ml MANNITOL | | | |
| 5 | 0.0151 | 0.0007 | 4.64 | 5 | 0.0238 | 0.00205 | 8.61 |
| 20 | 0.0063 | 0.00105 | 16.7 | 20 | 0.0119 | 0.00057 | 4.8 |
| 40 | 0.0021 | 0.00026 | 12.67 | 40 | 0.0073 | 0.00111 | 15.29 |
| 60 | 0.0015 | 0.00038 | 25.32 | 60 | 0.0047 | 0.00107 | 22.93 |

TABLE 4-continued

30% Relative Humidity, Reduced Cycle

| EtO Min | MEAN | STDEV | % ST DEV | EtO Min | MEAN | STDEV | % ST DEV |
|---|---|---|---|---|---|---|---|
| 20 mg/ml CARNOSINE | | | | 20 mg/ml ERYTHRITOL | | | |
| 5 | 0.0354 | 0.00229 | 6.46 | 5 | 0.0213 | 0.00262 | 12.31 |
| 20 | 0.0268 | 0.0024 | 8.97 | 20 | 0.022 | 0.00231 | 10.5 |
| 40 | 0.0233 | 0.00475 | 20.46 | 40 | 0.019 | 0.00226 | 11.91 |
| 60 | 0.028 | 0.0009 | 3.23 | 60 | 0.0196 | 0.00207 | 10.54 |

TABLE 5

30% Relative Humidity, Reduced Cycle

| EtO Min | MEAN | STDEV | % ST DEV | Eto Min | MEAN | STDEV | % ST DEV |
|---|---|---|---|---|---|---|---|
| NO ADDITIVES | | | | 20 mg/ml SORBITOL | | | |
| 5 | 0.0152 | 0.00184 | 12.11 | 5 | 0.0145 | 0.00087 | 6.02 |
| 20 | 0.0043 | 0.00038 | 8.73 | 20 | 0.006 | 0.00047 | 7.81 |
| 40 | 0.0016 | 0.00022 | 13.5 | 40 | 0.0023 | 0.00015 | 6.45 |
| 60 | 0.0011 | 0.00072 | 68.5 | 60 | 0.0011 | 0.00015 | 13.33 |
| 20 mg/ml TREHALOSE | | | | 20 mg/ml INOSITOL | | | |
| 5 | 0.0221 | 0.00307 | 13.91 | 5 | 0.0271 | 0.00316 | 11.67 |
| 20 | 0.0211 | 0.00457 | 21.66 | 20 | 0.0151 | 0.00253 | 16.76 |
| 40 | 0.0224 | 0.00532 | 23.78 | 40 | 0.0149 | 0.00402 | 26.95 |
| 60 | 0.0213 | 0.00099 | 4.57 | 60 | 0.0099 | 0.00292 | 29.55 |

As indicated in Tables 4 and 5, exposing spores with no additives to EtO at a reduced cycle gave lower LRV values and much steeper slopes of the response curves. This result was opposite of that expected for a reduced cycle. When spores were preconditioned with various additives, the LRV responses to the reduced cycles were much higher, with the exception of sorbitol, and the slopes of the response curves were much less steep than in a normal cycle, indicating failure. D-sorbitol was least effective while while trehalose and L-carnosine were most effective. D-inositol and D-mannitol were between the two extremes. It was surprising that trehalose provided the protection against EtO at 30% RH because it had the opposite effect at 60% RH. These results indicated that some of the polyhydroxyalcohols, the disaccharide trehalose and the dipeptide L-carnosine were useful as additives for spore preconditioning to modify EtO resistance in the manner described.

Example 6

Increase in Spore Resistance with Combinations of Mannitol, Trehalose, and Sorbitol This example describes the technique of pretreating or preconditioning spores to obtain the desired spore resistance to EtO in a standard cycle and to indicate failure in a reduced cycle. Combinations of additives were necessary in order to get the desired LRV response at a D value of about 3. Combinations of D-mannitol (M), myo-inositol (I), trehalose (T) and D-sorbitol (S) were used to obtain an optimum LRV response at normal and reduced sterilization cycles and a D value of about 3. Ideally, D-value and ROR determinations are calculated between 30% and 80% survival, but can be calculated even at 10% survival if the sample size is sufficiently large. The minimum sample size at 10% survival needs to be 44 in order to obtain an accurate D value. Spicher, G., Zbl. Hyg., 194:223–235, (1993). The cuvettes for LRV determinations and D value determinations were not the same but did contain spores from the same spore suspension with or without the additives and were exposed to EtO in the same Joslyn Gas B.I.E.R. vessel on the same day and at the same time, when exposure times allowed this.

When various combinations of trehalose and myo-inositol were added to spore suspensions before drying and exposing to EtO, the resistance of the spores to EtO at reduced cycles (30% relative humidity) was increased. It was observed that inositol was too strong (D values >3.5) in increasing the resistance of spores to EtO. This activity could not be overcome with addition of compounds that decreased resistance, such as trehalose, without decreasing the LRV response of the spores to undesirably low levels. Adding D-sorbitol, a compound that normally gives only a slight decrease in resistance, drastically reduced resistance and the germination rate when added to the spores in combination with trehalose at certain concentrations. This effect could be counteracted by adding D-mannitol. D-sorbitol was used primarily for enhancing the resuspension of the dried spores after EtO exposure because by itself, it only had a slight inhibitory effect on spore resistance.

Figure 7:
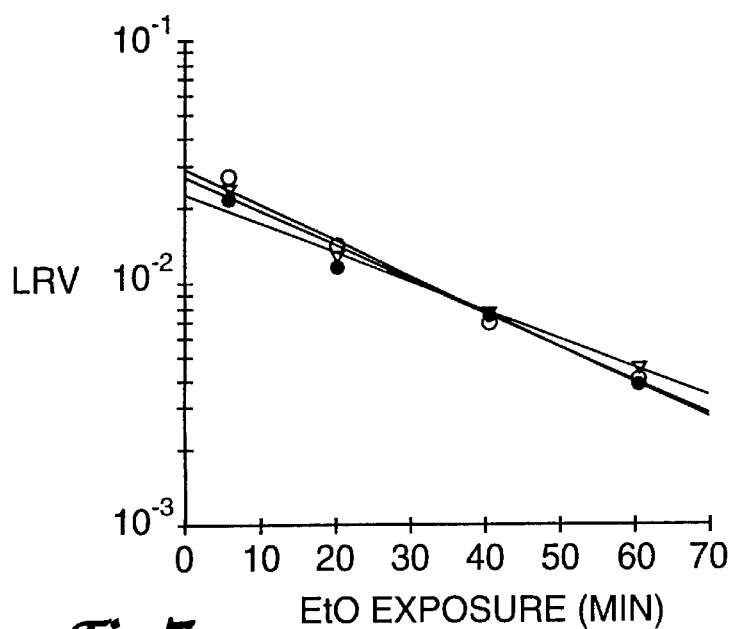
FIG. 7 is a graph that depicts the LRV of spores dried in the presence of 16 mg/ml D-sorbitol (open circles), 9 mg/ml D-mannitol, 8 mg/ml trehalose and 9 mg/ml D-sorbitol (filled circles) and 8 mg/ml D-mannitol, 8 mg/ml trehalose and 8 mg/ml D-sorbitol (open triangles) and subsequently exposed to a standard EtO cycle.
Figure 8:
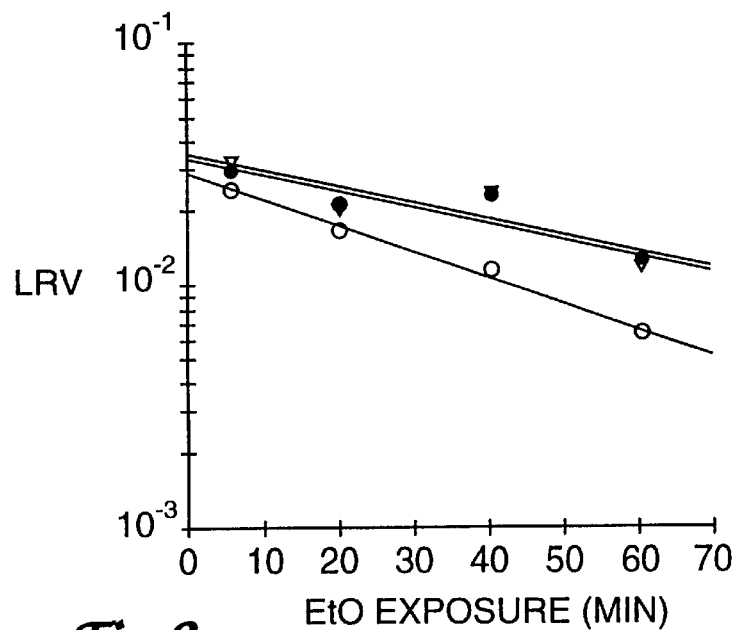
FIG. 8 is a graph that depicts the LRV of spores dried in the presence of 16 mg/ml D-sorbitol (open circles), 9 mg/ml D-mannitol, 8 mg/ml trehalose and 9 mg/ml D-sorbitol (filled circles) and 8 mg/ml D-mannitol, 8 mg/ml trehalose and 8 mg/ml D-sorbitol (open triangles) and subsequently exposed to a reduced cycle.

It was found that addition of D-mannitol (which is weaker than myo-inositol), trehalose and D-sorbitol together to spores produced the desirable results. Optimal concentrations of D-mannitol, trehalose, and D-sorbitol were determined after running 21 EtO experiments at 60% and 30% relative humidity. It appeared that each compound was doing something specific and distinct to change the resistance of spores to EtO. Interaction of the compounds was concentration dependent. It was determined that better results were obtained when the concentration of D-sorbitol was greater than 7 mg/ml but less than 9 mg/ml, the D-mannitol concentration was at least 8 mg/ml and the total concentration of additives was between 20 mg/ml and 30 mg/ml. In general, about 8 mg/ml of D-sorbitol and concentrations of D-mannitol and trehalose from about 7 mg to about 10 mg/ml gave optimal results as long as the concentration of trehalose was never greater than the concentration of D-mannitol. Tables 6 and 7, covering 60% and 30% RH respectively, show results obtained when optimal concentrations of D-mannitol+trehalose+D-sorbitol (M+T+S) were used. Preferred concentrations (mg/ml) of M, T, and S were found to be 8M+7T+8S, 8M+8T+8S, 9M+8T+8S, 9M+9T+8S and 9M+8T+9S. FIGS. 7 and 8 illustrate the types of LRV responses obtained after preconditioned spores were exposed to EtO in cuvettes at 60% RH and 30% RH, respectively. Table 8 shows the ROR and D values of B. subtilis spores with and without preconditioning with combinations of M, T, S and myo-inositol (I). The percent survival and D values were based on a sample size of 50 cuvettes with spores per experiment. The total # BIs is the sum of all the experiments. The optimum combinations gave D values of the preconditioned spores of 3.1±0.1, the desired level of resistance as measured by spore viability.

TABLE 6

60% Relative Humidity, Standard Cycle

| EtO Min | MEAN | ST DEV | % ST DEV |
|---|---|---|---|
| 16 mg SORBITOL/ml spores | | | |
| 5 | 0.0196 | 0.00058 | 2.95 |
| 20 | 0.0093 | 0.00042 | 4.49 |
| 40 | 0.0055 | 0.00054 | 9.99 |
| 60 | 0.0028 | 0.00017 | 6.15 |

TABLE 6-continued

60% Relative Humidity, Standard Cycle

| EtO Min | MEAN | ST DEV | % ST DEV |
|---|---|---|---|
| 8 mg MANNITOL + 7 mg TREHALOSE + 8 mg SORBITOL/ml spores | | | |
| 5 | 0.0229 | 0.002 | 8.71 |
| 20 | 0.0152 | 0.00073 | 4.79 |
| 40 | 0.0082 | 0.00093 | 11.33 |
| 60 | 0.0047 | 0.00048 | 10.31 |
| 8 mg MANNITOL + 8 mg TREHALOSE + 8 mg SORBITOL/ml spores | | | |
| 5 | 0.02 | 0.00053 | 2.65 |
| 20 | 0.0129 | 0.00097 | 7.58 |
| 40 | 0.0075 | 0.00132 | 17.76 |
| 60 | 0.0037 | 0.00029 | 7.71 |
| 9 mg MANNITOL + 8 mg TREHALOSE + 9 mg SORBITOL/ml spores | | | |
| 5 | 0.0191 | 0.00187 | 9.81 |
| 20 | 0.0115 | 0.00128 | 11.19 |
| 40 | 0.0075 | 0.00079 | 10.55 |
| 60 | 0.0048 | 0.00045 | 9.32 |
| 9 mg MANNITOL + 9 mg TREHALOSE + 8 mg SORBITOL/ml spores | | | |
| 5 | 0.0164 | 0.00136 | 8.3 |
| 20 | 0.0093 | 0.00051 | 5.62 |
| 40 | 0.0043 | 0.00026 | 6.08 |
| 60 | 0.0024 | 0.00036 | 14.83 |

TABLE 7

30% Relative Humidity, Reduced Cycle

| EtO Min | MEAN | ST DEV | % ST DEV |
|---|---|---|---|
| 16 mg SORBITOL/ml spores | | | |
| 5 | 0.0172 | 0.00102 | 5.95 |
| 20 | 0.0124 | 0.00093 | 7.47 |
| 40 | 0.0072 | 0.00041 | 5.77 |
| 60 | 0.0053 | 0.00047 | 8.87 |
| 8 mg MANNITOL + 7 mg TREHALOSE + 8 mg SORBITOL/ml spores | | | |
| 5 | 0.0401 | 0.00176 | 4.39 |
| 20 | 0.0361 | 0.00363 | 10.03 |
| 40 | 0.0304 | 0.00296 | 9.73 |
| 60 | 0.0258 | 0.00239 | 9.26 |
| 8 mg MANNITOL + 8 mg TREHALOSE + 8 mg SORBITOL/ml spores | | | |
| 5 | 0.0384 | 0.0011 | 2.88 |
| 20 | 0.0366 | 0.00135 | 3.69 |
| 40 | 0.0326 | 0.0009 | 2.78 |
| 60 | 0.0271 | 0.00236 | 8.72 |
| 9 mg MANNITOL + 8 mg TREHALOSE + 9 mg SORBITOL/ml spores | | | |
| 5 | 0.0358 | 0.00226 | 6.31 |
| 20 | 0.0358 | 0.00283 | 7.93 |
| 40 | 0.0318 | 0.00062 | 1.94 |
| 60 | 0.0253 | 0.00133 | 5.25 |
| 9 mg MANNITOL + 9 mg TREHALOSE + 8 mg SORBITOL/ml spores | | | |
| 5 | 0.0385 | 0.00209 | 5.43 |
| 20 | 0.0376 | 0.00148 | 3.95 |
| 40 | 0.0318 | 0.00152 | 4.79 |
| 60 | 0.0274 | 0.00041 | 1.5 |

As shown in Table 8, an unexpected finding of these studies was that preconditioning of the spores with D-mannitol, myo-inositol, and trehalose consistently gave ROR percentages much higher than that for untreated spores. At day one of growth after EtO exposure, the ROR (ROR-1) of M+T+S preconditioned spores was almost always 100% while at day two of growth, the ROR-2 was always 100%, regardless of the percent survival. The untreated controls (0) rarely showed a ROR of 100%. Since it is required that ROR must be 97% or greater when a BI is designated as giving reliable readings at less than 7 days of growth, the increased ROR at day two of growth due to preconditioning of spores, would be very useful for various biological indicators based on spore outgrowth. In addition, these results indicate that read-out time can be shortened to less than two days.

TABLE 8

| Treatment | Total # BIs | % Survival | ROR-1 | ROR-2 | D value |
|---|---|---|---|---|---|
| 0 | 400 | 32–90 | 78.1 | 96.4 | 1.8–2.0 |
| S | 500 | 18–90 | 53 | 84 | 1.65–1.8 |
| M + T + S | 1600 | 2–90 | 96.2 | 100 | 2.6–3.2 |
| I + T + S | 150 | 80–90 | 100 | 100 | 3.6–5.2 |

Example 7

Hydrogen Peroxide Plasma (HPP) Sterilization

HPP sterilization is a relatively low temperature (50° C.) method introduced as an alternative to EtO sterilization that is particularly useful for medical devices that may be sensitive to higher temperatures or to EtO. It has the advantage of being faster (75 minutes) than EtO (2 hours or more).

Preliminary work indicated that the best candidate for increasing the resistance of $B.\ subtilis$ spores to HPP was myo-inositol. The LRVs for myo-inositol after exposure for 3 and 20 minutes were 0.0332 and 0.01 respectively. Since complete spore sterilization gave an LRV of 0.0006, it appears that the dose response curve was more or less linear from 0–44 minutes of exposure to hydrogen peroxide. Other compounds that were equally effective against EtO had little or no effect against HPP. The M+T+S combination, L-carnosine and other individual compounds did not increase the resistance of the $B.\ subtilis$ spores to plasma hydrogen peroxide as much as desired.

Concentrations of myo-inositol and D-mannitol ranging from 5 to 20 mg/ml and combinations of the two were tried. Depending on the concentration of these two additives, it was possible to get from zero to 100% resistance of the LRV response of spores to HPP sterilization. Other cyclitols such as D-sorbitol decreased resistance, even at low concentrations of 1–2 mg/ml. Meso-erythritol and adonitol were even more effective in lowering the resistance of the spores to HPP than sorbitol. It appeared from these experiments that a combination of inositol and mannitol was probably best although adding very small amounts of erythritol may be useful in optimizing the spore preconditioning formulations.

It was found, however, that the LRV response of $B.\ subtilis$ spores, preconditioned with myo-inositol/D-mannitol, as a function of HPP exposure time was not linear in most experiments and the error within treatments was often greater than 20%. This suggested that there may be considerable residual hydrogen peroxide ($H_2O_2$) left behind in the spores after a normal 75 minute cycle, and even more when the cycle was interrupted during the diffusion phase. Catalase, which decomposes $H_2O_2$ into oxygen and water, can be used to remove the excess $H_2O_2$ from the spores after a sterilization cycle. See, for example, U.S. Pat. No. 5,552,320. After removal of the cuvettes from the sterilizer, 100 μl of each catalase dilution (catalase:water) were added to each cuvette and allowed to react for at least 10 minutes before adding the germination medium. LRV determinations were as per standard procedure described earlier. Table 9 summarizes the results obtained from spores preconditioned with 10 mg/ml D-mannitol, 5 mg/ml myo-inositol and 0.5 mg/ml meso-erythritol, sterilized with hydrogen peroxide plasma and then incubated with different concentrations of catalase. Table 10 summarizes the results from a similar experiment in which spores were pre-conditioned with 10 mg/ml mannitol, 5 mg/ml inositol and 1 mg/ml erythritol.

Without additives, *B. subtilis* spores exposed to even 2 minutes of hydrogen peroxide were killed. When catalase was used with the *B. subtilis* spores preconditioned with inositol/mannitol/and a trace amount of erythritol, a more or less linear LRV response was obtained with a steep (greater than 0.02) negative slope was obtained as a function of the time of exposure to HPP. Thus, the feasibility of using the LRV bioassay with preconditioned *B. subtilis* spores in a BI for HPP sterilization was demonstrated.

Example 8

Steam Sterilization

The organism most commonly used to monitor the effectiveness of steam sterilization are spores of the thermophilic bacterium *B. stearothermophilus*. Additives that were found to be effective in changing the sensitivity of *B. subtilis* spores were used to precondition *B. stearothermophilus* spores and then the effectiveness of steam sterilization was monitored.

Trehalose (Tre), myo-inositol (Inos), D-mannitol (Man), D-sorbitol (Sorb), and L-carnosine (Carn) were added to suspensions of *B. stearothermophilus* spores in sterile deionized water at the concentrations (mg/ml) indicated in Table 11. For example, the column labeled Tre 10 represents 10 mg/ml of trehalose. Twenty microliter aliquots of the treated spore suspensions, approximately $10^6$ spores, were then deposited on standard paper strips (Schleicher & Schuell 591A) and dried overnight at 37° C. The coated paper strips were then used to assemble the 3M Attest 1292 Biological Indicator. See, U.S. Pat. No. 4,883,641. Three BIs were used at each exposure using a standard 121° C. prevacuum cycle in a Getinge Steam Sterilizer, followed by an exposure cycle consisting of a 4 pulse prevacuum with a vacuum level of 0.070 bars and a steam charge level of 1.0 bars with each pulse. After exposure, the indicators were crushed to release the growth medium contained within an ampule in the BI and incubated at 60° C. for seven days. At the end of seven days, the BIs were checked to determine how many were positive for growth as indicated by a color change in the pH indicator dye, bromocresol purple, from purple to yellow. A range of several different exposure times were used covering incomplete to complete sterilization, as can be seen from the control spores prepared without additives. The data presented are from experiments with one crop of spores. Similar results were observed when other crops of *B. stearothermophilus* spores were used.

TABLE 9

| Exposure Min. | LRV-1 | LRV-2 | LRV-3 | LRV-4 | MEAN | ST. DEV. |
|---|---|---|---|---|---|---|
| 1:200 catalase | | | | | | |
| 0 | 0.0581 | 0.0569 | 0.0588 | 0.0586 | 0.0581 | 0.00085 |
| 3 | 0.0184 | 0.0153 | 0.0211 | 0.0022 | 0.0183 | 0.00837 |
| 10 | 0.0193 | 0.0168 | 0.0044 | 0.0076 | 0.0076 | 0.01203 |
| 25 | 0.0067 | 0.0023 | 0.0012 | | 0.0034 | 0.00291 |
| 45 | 0.0022 | 0.0008 | 0.0015 | 0.0009 | 0.0014 | 0.00064 |
| 1:400 catalase | | | | | | |
| 0 | 0.0568 | 0.0573 | 0.0547 | 0.0557 | 0.0561 | 0.00116 |
| 3 | 0.0091 | 0.0139 | 0.0131 | 0.0161 | 0.0131 | 0.00292 |
| 10 | 0.0043 | 0.011 | 0.0092 | 0.0074 | 0.0079 | 0.00286 |
| 25 | 0.0064 | 0.0027 | 0.0017 | 0.0021 | 0.0022 | 0.00050 |
| 45 | 0.0018 | 0.0029 | 0.0008 | 0.0003 | 0.0015 | 0.00115 |

TABLE 10

| Exposure min. | LRV-1 | LRV-2 | LRV-3 | LRV-4 | MEAN | ST DEV | % ST DEV |
|---|---|---|---|---|---|---|---|
| 1:40 catalase | | | | | | | |
| 0 | 0.056 | 0.0566 | 0.0571 | 0.0531 | 0.0557 | 0.00179 | 3.2149 |
| 5 | 0.017 | 0.0179 | 0.0134 | 0.0055 | 0.0161 | 0.00238 | 14.7899 |
| 25 | 0.0022 | 0.0019 | 0.0033 | 0.0014 | 0.0022 | 0.00080 | 36.5525 |
| 45 | 0.0029 | 0.0021 | 0.0014 | 0.003 | 0.00235 | 0.00075 | 31.9385 |
| 1:200 catalase | | | | | | | |
| 0 | 0.0557 | 0.0553 | 0.0545 | 0.0552 | 0.05518 | 0.00049 | 0.9047 |
| 5 | 0.0186 | 0.0147 | 0.0109 | 0.0123 | 0.01413 | 0.00337 | 23.8643 |
| 25 | 0.0008 | 0.0021 | 0.0027 | 0.0019 | 0.00223 | 0.00042 | 18.6418 |
| 45 | 0.0002 | 0.0017 | 0.0004 | 0.0024 | 0.00118 | 0.00105 | 89.6315 |
| 1:400 catalase | | | | | | | |
| 0 | 0.054 | 0.0536 | 0.0543 | 0.0602 | 0.05397 | 0.00313 | 5.7996 |
| 5 | 0.0122 | 0.0139 | 0.0122 | 0.0087 | 0.01277 | 0.00219 | 17.1193 |
| 25 | 0.0045 | 0.0033 | 0.002 | 0.0033 | 0.00328 | 0.00102 | 31.1765 |
| 45 | 0.002 | 0.001 | 0.0015 | 0.0011 | 0.0014 | 0.00045 | 32.4719 |

As shown in Table 11, L-carnosine very effectively increased the resistance of *B. stearothermophilus* spores to steam sterilization. The other additives tested appeared to have no effect. As little as 2 mg of L-carnosine/ml of spores provided commmplete resistance to steam sterilization at exposure times that killed untreated spores. L-carnosine was also one of the most effective additives for increasing the resistance of *B. subtilis* spores to EtO as shown in previous examples.

TABLE 11

| Exp Min | Control | Tre 10 | Tre 20 | Inos 10 | Inos 20 | Man 10 | Man 20 |
|---|---|---|---|---|---|---|---|
| 6 | 3 | 3 | 3 | 3 | 3 | 3 | 3 |
| 8 | 3 | 3 | 3 | 3 | 3 | 3 | 3 |
| 10 | 3 | 2 | 3 | 2 | 3 | 3 | 3 |
| 12 | 0 | 0 | 0 | 0 | 0 | 1 | 0 |
| 14 | 0 | 0 | 0 | 0 | 0 | 1 | 0 |

| Min | Sorb 30 | Carn 1 | Carn 2 | Carn 5 | Carn 10 | Carn 20 |
|---|---|---|---|---|---|---|
| 7 | 3 | — | — | — | 3 | 3 |
| 9 | 3 | 3 | — | 3 | 3 | 3 |
| 10 | — | 3 | 3 | 3 | — | — |
| 11 | 2 | 3 | 3 | 3 | 3 | 3 |
| 12 | — | 1 | 3 | 3 | — | — |
| 13 | 1 | 0 | 3 | 2, 3 | 3 | 3 |
| 15 | 0 | — | — | — | 3 | 3 |
| 20 | — | — | — | — | — | 2 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. Microbial spores comprising an additive specifically bound to sterilant-sensitive sites in said spores, wherein said additive increases sensitivity of said spores to a sterilant.

2. The spores of claim 1, wherein said additive is an oligosaccharide.

3. The spores of claim 2, wherein said oligosaccharide is selected from the group consisting of trehalose, raffinose, melibiose and maltose.

4. The spores of claim 3, wherein said oligosaccharide is trehalose.

5. The spores of claim 1, wherein said additive increases read-out reliability of a biological indicator containing said spores.

6. The spores of claim 5, wherein said additive shortens read-out time to less than two days.

7. Microbial spores comprising a dipeptide specifically bound to sterilant-sensitive sites in said spores, said dipeptide altering sensitivity of said spores to a sterilant.

8. The spores of claim 7, wherein said spores are dried.

9. The spores of claim 7, wherein said dipeptide is stereospecifically bound to sterilant-sensitive sites in said spores.

10. The spores of claim 7, wherein said dipeptide decreases the sensitivity of said spores to said sterilant.

11. The spores of claim 7, wherein said dipeptide increases the linear reaction velocity of said spores.

12. The spores of claim 7, wherein said dipeptide increases read-out reliability of a biological indicator containing said spores.

13. The spores of claim 12, wherein said dipeptide shortens read-out time to less than two days.

14. The spores of claim 7, wherein said sterilant is selected from the group consisting of steam, ethylene oxide, radiation, heat, sodium hypochlorite, polyvinylpyrrolidone-iodine, sodium dichlorocyanurate, low temperature steam-formaldehyde, glutaraldehyde, hydrogen peroxide, hydrogen peroxide plasma, peracetic acid and mixtures thereof.

15. The spores of claim 7, wherein said sterilant comprises ethylene oxide.

16. Microbial spores comprising two or more additives specifically bound to sterilant-sensitive sites in said spores, said additives increasing sensitivity of said spores to a sterilant.

17. The spores of claim 16, wherein said additives are effective for use during ethylene oxide sterilization in a standard cycle.

18. The spores of claim 16, wherein said additives are effective for use during ethylene oxide sterilization in a reduced cycle.

19. The spores of claim 17 or claim 18, wherein said additives comprise mannitol, trehalose and sorbitol.

20. The spores of claim 16, wherein said sterilant comprises hydrogen peroxide plasma.

21. The spores of claim 20, wherein said additives comprise inositol and mannitol.

22. The spores of claim 21, wherein said additives further comprise erythritol.

23. The spores of claim 16, wherein said additives increase read-out reliability of a biological indicator containing said spores.

24. The spores of claim 23, wherein said additives shorten read-out time to less than two days.

25. The spores of claim 7 or claim 16, wherein said spores are *Bacillus subtilis* spores.

26. The spores of claim 7 or claim 16, wherein said spores are *Bacillus stearothermophilus* spores.

27. A method for increasing the sensitivity of microbial spores to a sterilant, said method comprising drying said spores in a liquid composition comprising an additive in an amount effective to increase sensitivity of microbial spores to a sterilant when said additive is specifically bound to sterilant-sensitive sites in said spores, wherein drying said spores occurs at a temperature between about 35° C. and about 55° C.

28. The method of claim 27, wherein said additive is an oligosaccharide.

29. The method of claim 28, wherein said oligosaccharide is selected from the group consisting of trehalose, raffinose, melibiose and maltose.

30. The method of claim 29, wherein said oligosaccharide is trehalose.

31. The method of claim 27, wherein said additive is selected from the group consisting of polyhydroxyalcohols and dipeptides.

32. The method of claim 31, wherein said additive is selected from the group consisting of inositol, sorbitol, mannitol, adonitol, erythritol and L-carnosine.

33. The method of claim 27, wherein said temperature is between about 45° C. and about 50° C.

34. The method of claim 27, wherein said additive increases read-out reliability of a biological indicator containing said spores.

35. The method of claim 34, wherein said additive shortens read-out time to less than two days.

36. A biological indicator comprising microbial spores and a solid support to which said spores are attached, said spores comprising two or more additives specifically bound to sterilant-sensitive sites in said spores, said additives increasing sensitivity of said spores to a sterilant.

37. A biological indicator comprising microbial spores and a solid support to which said spores are attached, said spores comprising a dipeptide specifically bound to sterilant-sensitive sites in said spores, said dipeptide altering sensitivity of said spores to a sterilant.

* * * * *